(12) United States Patent
Shiozawa et al.

(10) Patent No.: US 7,615,341 B2
(45) Date of Patent: Nov. 10, 2009

(54) DISEASE SUSCEPTIBILITY GENE FOR RHEUMATOID ARTHRITIS, PROTEIN THEREOF, EVALUATION METHOD AND EVALUATION KIT FOR EVALUATING ONSET POSSIBILITY OF RHEUMATOID ARTHRITIS BY USING THOSE, AND REMEDY AND CURING MEDICINE FOR RHEUMATOID ARTHRITIS

(75) Inventors: Shunichi Shiozawa, 11-6, Takenodai 2-chome, Nishi-ku, Kobe-shi, Hyogo 651-2274 (JP); Koichiro Komai, Kobe (JP); Mikiko Nakatsukasa, Asaguchi-gun (JP)

(73) Assignee: Shunichi Shiozawa, Hyogo (JP)

( * ) Notice: Subject to any disclaimer, the term of this patent is extended or adjusted under 35 U.S.C. 154(b) by 145 days.

(21) Appl. No.: 10/501,259

(22) PCT Filed: Jan. 8, 2003

(86) PCT No.: PCT/JP03/00089

§ 371 (c)(1),
(2), (4) Date: Jul. 9, 2004

(87) PCT Pub. No.: WO03/060126

PCT Pub. Date: Jul. 24, 2003

(65) Prior Publication Data

US 2005/0176004 A1  Aug. 11, 2005

(30) Foreign Application Priority Data

Jan. 11, 2002  (JP)  ............................. 2002-005326

(51) Int. Cl.
*C12Q 1/68* (2006.01)
*C07H 21/04* (2006.01)
*C12P 19/34* (2006.01)

(52) U.S. Cl. ........................... 435/6; 536/24.3; 435/91.2

(58) Field of Classification Search ........................ None
See application file for complete search history.

(56) References Cited

U.S. PATENT DOCUMENTS

| | | | |
|---|---|---|---|
| 6,623,924 B1 | 9/2003 | Shiozawa | |
| 2002/0123054 A1* | 9/2002 | Hillman et al. | ................ 435/6 |
| 2004/0013655 A1 | 1/2004 | Shiozawa et al. | |

FOREIGN PATENT DOCUMENTS

| | | | | |
|---|---|---|---|---|
| EP | 1 008 648 A1 | 6/2000 | | |
| EP | 1 164 190 A1 | 12/2001 | | |
| WO | WO 96/11269 | * | 4/1996 | ................ 435/6 |
| WO | WO-96/11269 A | | 4/1996 | |
| WO | WO 96/20213 | | 7/1996 | |
| WO | WO 96/31598 | | 10/1996 | |
| WO | WO 00/02587 | | 1/2000 | |
| WO | WO 00/64946 | | 11/2000 | |
| WO | WO 02/055692 A2 | | 7/2002 | |

OTHER PUBLICATIONS

Davis, et al., Cell (1996) vol. 87, pp. 1161-1169.*
Davis, et al, Cell, (1996) vol. 87, pp. 1161-1169.*
Wu, Journal of pathology (2001) vol. 195, pp. 53-65.*
Newton et al, Journal of computational biology (2001) vol. 8, pp. 37-52.*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Shiozawa et al (Nippon Rinsho (2002) vol. 60, pp. 2269-2275)(translation pp. 1-19).*
Ioannidis (PLOS Med vol. 2, issue 8, e 124, pp. 0696-00701).*
Davis et al., "Human angiopoietin-1 mRNA, complete cds.", Database GenBank Accession No. U83508 (Mar. 26, 1997).
Shiozawa et al., "Studies on the pathogenesis of autoimmune diseases from the viewpoint of the disease susceptibility genes" 21(1)30-35 (2003).
Shiozawa et al., "The molecular genetics of rheumatoid arthritis disease gene", p. 2269-2275 (2002).
Shiozawa et al., "Identification of the gene loci that predispose to rheumatoid arthritis", Int'l Immunology 10(12):1891-1895 (1998).
Shiozawa et al., "An approach to identify new genes in autoimmune diseases: lessons from rheumatoid arthritis", Ref. Immunogenet., 2(1):133-139 (2000).
Shei Ishikawa, "How to diagnose Rheumatoid Arthritis", Remedy, 73(3):23-27 (1991).
Edward D. Harris, Jr., "Rheumatoid Arthritis Pathophysiology and Implications for Therapy", The New England Journal of Medicine 322(18):1277-1289 (1990).
Vyse et al., "Genetic Analysis of Autoimmune Disease", Cell, 85:311-318 (1996).
Alisa Erika Koch, "The role of Angiogenesis in rheumatoid arthritis: recent developments", Ann. Rheum. Dis.59(suppl. I) pp. i65-i71 (2000).
Thurston et al., Angiopoietin-1 protects the adult vasculature against plasma leakage, Nature Medicine, 6(4):460-463 (2000).
Masato Nose, "Origin of the Diversity and Similarity of Pathological Manifestations of Collagen Disease", Ryumachi, 40(5):833-848 (2000).
Yamamoto et al., "Study on GEM as Causative Gene for Rheumatoid Arthritis (RA)", Ryumachi, 39:445 (1999).

(Continued)

*Primary Examiner*—J D Schultz
*Assistant Examiner*—Steven C Pohnert
(74) *Attorney, Agent, or Firm*—Edwards Angell Palmer & Dodge LLP; David G. Conlin; Mark D. Russett

(57) ABSTRACT

An gene was identified as a RA disease susceptibility gene on Human Chromosome 8, the gene coding a protein that has an amino acid sequence shown in SEQ. ID NO. 1 and that has such mutation that glycine is inserted as a 269th amino acid in the sequence. Moreover, it was found that mutation of the gene and the protein relate to onset of RA. Achieved is a method of evaluating with high accuracy the onset or onset possibility of RA by using the mutation.

2 Claims, 4 Drawing Sheets

OTHER PUBLICATIONS

Davis et al., "Isolation of Angiopoietin-1, a Ligand for the TIE2 Receptor, by Secretion-Trap Expression Cloning", Cell, 87:1161-1169.

Kruglyak et al., Complete Multipoint Sib-Pair Analysis of Qualitative and Quantitative Traits, Am. J. Hum. Genet., 57:439-454 (1995).

Hasegawa et al., "Novel Smooth Muscle Cell Lines form Transgenic Mice Harboring Temperature-sensitive SV40 Larch T-antigen Gene. Temperature dependent Expression of Smooth Muscle Myosin Heavy Chain-1 and Calponin Genes", J. Mol. Cell Cardiol., 29:2177-2186 (1997).

Cheung A.H. et al., "Endothelial Tie2/Tek Ligands Angiopoietin-1 (ANGPT1) and Angiopoietin-2 (ANGPT2): Regional Localization of the Human Genes to 8q22.3-q23 and 8p23." *Genomics*, Academic Press, San Diego, US, vol. 48, No. 3, Mar. 15, 1998, pp. 389-391, XP004449220.

Bernhard Witzenbichler et al. "Chemotactic Properties of Angiopoietin-1 and -2, Ligands for the Endothelial-specific Receptor Tyrosine Kinase Tie2", The Journal of Biological Chemistry, vol. 273, No. 29, Issue of Jul. 17 pp. 18514-18521, 1998.

Michael J. Hansbury et al. "Production and characterization of a Tie2 agonist monoclonal antibody", Angiogenesis 4, pp. 29-36, 2001.

Examiner's first report on patent application No. 2003201847 by Shunichi Shlozawa.

Uchida et al., "Immunohistochemical localisation of protein tyrosine kinase receptors Tie-1 and Tie-2 in synovial tissue of rheumatoid arthritis: correlation with angiogenesis and synovial proliferation", Ann. Rheum. Dis., vol. 59, pp. 607-614 (2000).

Scola et al., "Expression of Angiogenic Factors in Juvenile Rheumatoid Arthritis", Arthritis & Rheumatism, vol. 44, No. 4, pp. 794-801 (2001).

\* cited by examiner

| marker | Z0 | Z1 | Z2 | Lod Score |
|---|---|---|---|---|
| D8S1762 | 0.25 | 0.50 | 0.25 | 0.00 |
| D8S521 | 0.18 | 0.36 | 0.46 | 0.54 |
| D8S1738 | 0.25 | 0.50 | 0.25 | 0.00 |
| D8S556 | 0.13 | 0.26 | 0.61 | 1.35 |
| D8S1830 | 0.16 | 0.31 | 0.53 | 0.84 |
| D8S539 | 0.23 | 0.45 | 0.32 | 0.07 |

| | n | nt805(del3)HOMO | nt805(del3)HETERO | nt805 HOMO |
|---|---|---|---|---|
| Familial RA | 69 | 53(76.8%) | 15(21.7%) | 1(1.5%) |
| Familial not RA | 28 | 20(71.4%) | 8(28.6%) | 0( 0%) |
| Sporadic RA | 225 | 170(75.5%) | 51(22.7%) | 4(1.8%) |
| Sporadic not RA | 383 | 353(92.2%) | 30( 7.8%) | 0( 0%) |

DISEASE SUSCEPTIBILITY GENE FOR RHEUMATOID ARTHRITIS, PROTEIN THEREOF, EVALUATION METHOD AND EVALUATION KIT FOR EVALUATING ONSET POSSIBILITY OF RHEUMATOID ARTHRITIS BY USING THOSE, AND REMEDY AND CURING MEDICINE FOR RHEUMATOID ARTHRITIS

TECHNICAL FIELD

The present invention relates to a disease susceptibility gene for rheumatoid arthritis and a use thereof. Specifically, the present invention provides a novel evaluation method and a novel evaluation kit, etc. for evaluating onset or onset possibility of rheumatoid arthritis, the novel evaluation method and evaluation kit, etc. characterized in detecting whether mutation of the gene or mutation of a protein that is translation product of the gene, is present or absent. Further, the present invention relates to a remedy and a curing medicine for the rheumatism.

BACKGROUND ART

Rheumatoid arthritis (hereinafter, may be referred to as just "RA"), whose main symptom is multiple erosive arthritis, is a systemic inflammatory disease whose cause is unknown and which affects multiple organs at once. RA develops chronically while alternating between remission and exacerbation, causes the damage and deformation of joints if left untreated, and finally shows the dysfunction of motor organs. In some cases, RA is life-threatening. Therefore, RA patients suffer physically and mentally from heavy pain all their lives.

RA shows a wide variety of symptoms. For the diagnosis of RA, the diagnostic criteria by the American College of Rheumatology have been widely used. However, the RA onset is slow and usually takes several weeks to several months. The percentage positive of a rheumatoid factor, which is used as an objective index in the diagnostic criteria adopted by the American College of Rheumatology, is about 33% within three months and about 88% in twelve months and longer (Treatment, Vol. 73, No. 3, pp23-27, in 1991), and a definite diagnosis of RA has not been achieved. Consequently, approaches to the diagnosis of rheumatoid arthritis have been made by detecting rheumatoid arthritis-related IgM antibodies in patient sera that react with a recombinant antigen (See Japanese Laid-Open Patent Publication No. 513257/1998 (Tokukaihei 10-513257) published on Dec. 15, 1998).

Further, in the therapy for RA, therapeutic measures to be selected usually differ depending on a progressing course in the condition of RA pathema. Generally, in an early stage when a definite diagnosis cannot be given, non-steroidal anti-inflammatory drug (NSAID) is administered. In the case when the definite diagnosis can be given, disease modifying anti-rheumatic drugs (DMARD) is administered in addition to NSAID. Especially in the early stage of the RA onset, a definite diagnosis is difficult to be given. Under the present circumstances, discrimination from other rheumatoid diseases including collagen disease is carried out together with a careful observation of the progress while NSAID is administered. When symptoms progress further, steroid drug may be administered, and a medical therapy for the enhancement of pain relief is carried out together with a physical therapy and an orthotic therapy for the maintenance and recovery of joint function. Furthermore, when the joint damage causes inconvenience in a daily life, a surgical therapy may be carried out.

Aspects of arthritis and joint damage causing RA, particularly the pathological courses thereof, have been elucidated gradually through various research works. RA is induced by the concomitant participation of numerous causative factors including living environment and is then exacerbated progressively to the stage of apparent diseases; therefore, the interactive mechanism per se of such numerous factors should be elucidated for accurate characterization and appropriate therapeutic management of the disease. The prevalence of RA is not more than 1% on a global scale (New England Journal of Medicine, Vol. 322, p. 1277-1289, in 1990), but the frequency of the disease is about 8 times greater in sibs of the patients with the disease (Cell, Vol. 85, p. 311-318, in 1996). Hence, it is predicted that a certain genetic factor may serve as one of the causative factors. Since an environment is regarded as one of the causative factors, previous knowledge of the RA onset possibility makes it possible to delay and prevent the RA onset by attentions to the diet, virus infection, stresses, etc. in daily life. Furthermore, an early diagnosis and a proper treatment in early stages can delay the course of RA and expect the improvement of prognosis.

In International Patent Publication WO98/51791 (published on Nov. 19, 1998), the inventors of the present application have conducted the linkage analysis using microsatellite markers to RA patients and their sibs and specified three loci where causative genes of rheumatoid arthritis are located. The following causative genes have been identified:

(1) A causative gene for rheumatoid arthritis, which gene is located within ±1 centimorgan on a DNA sequence on human chromosome 1 to which the microsatellite markers D1S214 and/or D1S253 are hybridized.

(2) A causative gene for rheumatoid arthritis, which gene is located within ±1 centimorgan on a DNA sequence on human chromosome 8 to which the microsatellite marker D8S556 is hybridized.

(3) A causative gene for rheumatoid arthritis, which gene is located within ±1 centimorgan on a DNA sequence on human chromosome X to which the microsatellite markers DXS1001, DXS1047, DXS1205, DXS1227 and/or DXS1232 are hybridized.

As described above, it was found that the loci of disease susceptibility genes of rheumatoid arthritis locate on chromosomes 1, 8, and X. Among the chromosomes, the disease susceptibility genes of RA have been identified for chromosomes 1 and X, but not for chromosome 8.

In the view of this, objects of the present invention is to identify the disease susceptibility genes of rheumatoid arthritis located on human chromosome 8, and to provide (i) an evaluation (diagnosing) method for evaluating onset or onset possibility of RA with high accuracy by detecting whether mutation of the gene or mutation of a protein that is translation product thereof, is present or absent, and (ii) evaluation (diagnosing) kit thereof. Another object of the present invention is to provide a remedy and a curing medicine effective for RA patients having mutation in the disease susceptibility gene for rheumatoid arthritis.

DISCLOSURE OF INVENTION

In view of the aforementioned objects, the inventor of the present invention carried out detailed gene mapping of human chromosome 8 by using a plurality of microsatellite markers, thereby identifying a locus of an RA-relating gene. Further, the inventor of the present invention studied on possibility whether Angiopoietin-1 gene located in a vicinity of the locus is an RA disease susceptibility gene. Through experiments, the inventor of the present invention found out the followings:

this gene has two types: 3-base-insertion type and 3-base-deletion type; there was a significant difference between a healthy subject and an RA patient, letting a homozygotes of the 3-base-deletion type be no mutation, and a heterozygotes and a homozygotes of the 3-base-insertion type be mutation; and an expression of mRNA in RA patients is significantly lower than in healthy subjects.

Based on those findings, the inventor of the present invention found out effectiveness of the evaluation (diagnosing) method and the evaluation (diagnosing) kit for evaluating onset or onset possibility of RA, and thereby accomplished the present invention. Further, the present invention is also effective as a novel remedy and a curing medicine for rheumatoid arthritis.

In the present specification, A, C, G, and T represent bases of adenine, cytosine, guanine, and thymine, respectively, unless otherwise stated. Further, amino acids and amino acid residues are expressed by a one-letter code or three-letter code defined by IUPAC and IUB.

A gene according to the present invention is a disease susceptibility gene for rheumatoid arthritis, the gene encoding a protein that has an amino acid sequence shown in SEQ. ID NO.1 and that has such mutation that glycine is inserted as a 269th amino acid in the sequence. Specifically, the gene according to the present invention may be, for example, Angiopoietin-1 gene having a base sequence shown in SEQ. ID NO. 2, and having such mutation that 3 bases "GGT" are inserted as 805th to 807th bases in the sequence. The 805th to 807th bases correspond to the 1114th to 1116th bases in the base sequence (Accession No. U83508) registered as the cDNA of Angiopoietin-1 gene in the gene bank.

The term "gene" includes polynucleotides such as, at least, genomic DNAs, cDNAs, mRNAs, and the like. Thus, the gene according to the present invention may be, besides cDNA of Angiopoietin-1 gene, (i) an mRNA having a base sequence corresponding to a base sequence of the cDNA, (ii) a genomic DNA from which the mRNA is transcribed, or (iii) the like. Moreover, the term "gene" indicates not only double-stranded DNAs, but also single-stranded (sense strand or anti sense strand) DNAs that constitute the double-stranded DNAs, or RNAs. Furthermore, the "gene" may contain a sequence of an untranslated region (UTR), a promoter sequence, a vector sequence (including an expression vector sequence), and the like sequence, besides a translation region.

A protein according to the present invention is a protein having an amino acid sequence shown in SEQ. ID NO.1, and having such mutation that glycine is inserted as a 269th amino acid in the sequence. The protein is a translation product of the aforementioned Angiopoietin-1 gene, and may further contain an additional polypeptide. Such a polypeptide is added, for example, in a case where this protein is tagged with an epitope by using a His tag or the like.

The aforementioned Angiopoietin-1 is a factor belonging to the Angiopoietin Family and is considered that it plays an important role in forming a blood vessel. angiogenesis-related tyrosine kinase type receptor has VEGF receptor family and TIE receptor family. It has been reported that VEGF is excessively produced in RA patients (see Ann Rheum Dis: 59: i65-71, 2000). It is known that Angiopoietin-1 is a ligand for TIE2 receptor and acts complementary with VEGF to suppress vessel damage and bleeding (see Nature Medicine: Vol. 6: 460-463: 2000). However, a relationship between Angiopoietin-1 and pathema has been poorly understood.

The inventor of the present invention found out a linkage at microsatellite marker D8S556 by conducting detailed gene mapping as described above. Because the finding agrees with a result of a linkage analysis previously conducted, the inventor of the present invention considers that this site is the locus of the RA disease susceptibility gene on human chromosome 8.

The aforementioned D8S556 is mapped in a long-arm region of human chromosome 8. This region corresponds to a region of chromosome 15 in mice. It has been reported that arthritis susceptibility gene loci Paam1 are present in the region of chromosome 15. (See "*Ryumachi*" 40(5): 833-848, 2000). Moreover, it has been found that D8S556 locates at 584.52-584.72cR (See "*Ryumachi*" vol. 39:P445, 1999). Angiopoietin-1 is mapped at 589.07cR in GB4 Map. Because of its location on the chromosomes, it is reasonable to consider Angiopoietin-1 as a candidate for a disease susceptibility gene.

Further, as a result of analysis on a gene isolated from synovial membranes and peripheral blood of RA patients, it was found out that there are two types of Angiopoietin-1 gene; 3-base-insertion type and 3-base-deletion type. Hereinafter, that site on a gene sequence, at which 3 base insertion and 3 base deletion occur, is referred to as a "mutation site". Similarly, that site on an amino acid sequence, at which glycine insertion and glycine deletion occur, is referred to as a "mutation site". The mutation site on the amino acid sequence corresponding to the mutation site on the gene sequence.

Note that it has also been reported the 3 base deletion occurs in human cell line T98G (see Cell. Vol. 87: 1161-1169, 1996).

Angiopoietin-1 enhances formation of blood vessel network by acting complementary with VEGF. Specifically, VEGF is an important promoting factor in angiogenesis and promotes migration and proliferation of endothelial cell. Then, a mature blood vessel is structured by forming a new vascular basement membrane. In fact, a blood vessel inducted by using only VEGF in an experiment was immature and easily causes bleeding. It has been reported that excess production of VEGF occurs in RA. (See Ann Rheum Dis: 59: i65-71, 2000). However, there is no report regarding Angiopoietin-1 under such condition. The inventor of the present invention compared RA patients and healthy subjects in terms of an amount of expressed Angiopoietin-1 mRNA, and found out that the amount of the expressed mRNA was significantly low in peripheral blood in the RA patients. This suggests that, in RA, proliferation of immature blood vessel possibly contributes to development of chronic inflammation that is caused by leakage of immune cells from blood.

As later described in details, a gene and a protein according to the present invention are of effective use in a novel evaluating method and a novel evaluation kit for evaluating the onset or onset possibility of RA.

(1) Method of Evaluating Onset or Onset Possibility of RA

Here, the method of present invention of evaluating the onset or onset possibility of RA (in other words, a method of diagnosing RA) will be explained below, discussing, in order, (i) a case where a genomic DNA is used as a gene according to the present invention, (ii) a case where an mRNA (cDNA) is used as the gene, and then (iii) a case where a protein according to the present invention is used.

(i) Case where Genomic DNA is Used

A present method of evaluating by using the genomic DNA may be carried out as below, for example.

Genome of a subject can be obtained from any cells of human by standard methods known in the art. For example, the genome may be obtained from a hair, any organs, a peripheral lymphocyte, a synovial cell and the like. Moreover, the genome may be obtained from a cell that has been obtained from the subject and then cultured thereafter to be multiplied.

Further, the genome thus obtained may be amplified before use. The amplification may be carried out by a gene amplification method usually carried out, such as the PCR (Polymerase Chain Reaction) method, NASBA (Nucleic Acid Sequence Based Amplification) method, TMA (Transcription-Mediated Amplification) method, SDA (Strand Displacement Amplification) method, and the like.

There is no particular limitation in how to evaluate whether the genome has a mutation or not. For example, the evaluation may be conducted by using the Allele Specific Oligonucleotide Probe method, Oligonucleotide Ligation Assay method, PCR-SSCP method, PCR-CFLP method, PCR-PHFA method, invader method, RCA (Rolling Circle Amplification) method, Primer Oligo Base Extension method, or the like method.

For example, detection as to whether the genome has a mutation or not, can be carried out by (i) amplifying a region containing the mutation site of the gene from the genome thereby obtaining a PCR product, (ii) subcloning the PCR product thus obtained, and then (iii) performing direct sequencing of the subcloned PCR product. Moreover, by using the mutation-site-containing region in a oligonucleotide probe, it is also possible to detect whether the genome has the mutation or not. The mutation-site-containing region is used in a oligonucleotide probe, for example, in case where a DNA chip is constituted by fixing, on a chip, an oligonucleotide including a base sequence containing the mutation site, and the DNA chip is used for detecting whether the mutation is present or absent. In this case, the oligonucleotide probe, including the mutation site therein, preferably has a length of 7 to 50 nucleotides or a length of 10 to 30 nucleotides, and more preferably has a length of 15 to 25 nucleotides.

Moreover, the detection as to whether the genome has the mutation or not may be conducted by performing the southern blotting or the like in order to detect a difference between genome fragments in terms of size, the genome fragments cleaved by using an appropriate restriction enzyme.

By performing the detection on the mutation in the genome in these ways, it is possible to diagnose, with high accuracy, the subject in terms of RA (to evaluate whether the subject has developed RA or has a possibility that the subject will develop RA). Specifically, as described later, a significant difference was found between the RA patients and the healthy subjects, where no mutation is found in homozygotes of three base deletion type but a mutation is found in heterozygotes and homozygotes of three base insertion type. Hence, it is judged that there is a low possibility for RA onset or RA onset possibility, when a homozygote of three base deletion type is detected. On contrary, it is judged that there is a high possibility for RA onset or RA onset possibility, when a heterozygote is detected, especially, when a homozygote of three base insertion type is detected.

Note that a primer and a probe used in the method of evaluating may be prepared by using a DNA synthesizer by standard methods known in the art.

(ii) Case where mRNA (cDNA) is Used

In case where the mRNA is used, the detection as to whether the mutation is present or absent may be carried out as follows, for example: a cDNA is prepared from the mRNA by reverse transcription, the mRNA extracted from a cell of a subject. Then, that region of the cDNA, which contains the mutation site is amplified. After that, the detection is carried out (i) by directly sequencing a base sequence of thus amplified fragment, (ii) by using a DNA chip, or (iii) by using the RFLP (Restriction Fragment Length Polymorphism) method.

There is no particular limitation in a primer to be used in the amplification of the region containing the mutation site. For example, amplification reaction in which a cDNA is used as a template may be performed by using the following combination of primers.

```
Sense Primer:
5'-GCTGGCAGTACAATGACAG-3'      (SEQ. ID NO.3)

Anti Sense Primer:
5'-TCAAAAATCTAAAGGTCGAAT-3     (SEQ. ID NO.4)
```

By detecting, in this way, whether the mRNA (cDNA) has the mutation or not, it is possible to diagnose, with high accuracy, the subject in terms of RA (to evaluate whether the subject has developed RA or has a possibility that the subject will develop RA).

An alternative method of evaluating the onset or onset possibility of RA by using the mRNA is to measure an amount of an expressed mRNA (that is, Angiopoietine-1 mRNA of 3-base-deletion type) derived from a disease susceptibility gene for RA, the gene having a base sequence that is as shown in SEQ. ID NO.2 and is not so mutated that 3 bases "GGT", which are Nos.805 to 807 bases in the sequence, are inserted.

More specifically speaking, the above method of evaluating is so arranged that a pair of threshold values 1 and 2 is set with respect to the amount of the expressed mRNA, the threshold value 1<the threshold value 2; if the amount of the expressed mRNA is equal to or less than the threshold value 1, it is judged that a subject has developed rheumatoid arthritis highly possibly or has a high possibility that the subject will develop rheumatoid arthritis in the future; and if the amount of the expressed mRNA is equal to or more than the threshold value 2, it is judged that a subject has developed rheumatoid arthritis unlikely or has a low possibility that the subject will develop rheumatoid arthritis in the future. It is possible to use the RT-PCT method or the like conventionally well known to measure the amount of the expressed mRNA for use in the method for evaluating the onset or the onset possibility of RA.

(iii) Case where the Protein is Used

In case where the protein prepared from the cell of the subject is used, a method of evaluating whether or not glycine is inserted in the mutation site in the amino acid sequence of SEQ. ID NO. 1 may be adopted. The detection as to whether glycine is inserted or not may be carried out by a general sequencing method for protein. For example, the detection of glycine may be carried out as follows: an antibody that recognizes only the glycine-insertion type protein is prepared, and then the detection of glycine is performed by using the ELISA method; a protein is isolated. Then, by using a protein sequencer, the mutation is detected in the isolated protein, which may be, if necessary, fragmented by using an enzyme or the like; mutation as to isoelectric point of an amino acid is detected; a difference in mass is detected by mass spectrometry. It is preferable to adopt the method in which the detection of glycine is performed by preparing the antibody that recognizes only the glycine-insertion type protein, and using the ELISA method.

By detecting, in this way, whether or not glycine is inserted in the mutation site, it is possible to diagnose, with high accuracy, the subject in terms of RA (to evaluate whether the subject has developed RA or has a possibility that the subject will develop RA). Specifically, as described later, a significant difference was found between the RA patients and the healthy subjects, where no mutation is found in homozygotes of three base deletion type but a mutation is found in heterozygotes and homozygotes of three base insertion type. Hence, it is judged that there is a low possibility for RA onset or RA onset possibility, when the glycine-insertion type protein is not detected (in other words, only glycine deleted type protein is detected). On contrary, it is judged that there is a high possibility for RA onset or RA onset possibility, when both types of proteins are detected, and especially when only the glycine-insertion type protein is detected.

(2) Evaluation Kit for Onset or Onset Possibility of RA

An evaluation kit for onset or onset possibility of RA (in other words, diagnosis kit for RA) is not particularly limited, provided that the kit includes the reagent for detection of the mutation, for example, the primer, probe, antibody, or the like. The kit may be so arranged to further include another reagent in combination with the reagent.

For example, a kit for detecting whether the genome or the mRNA (cDNA) has the mutation or not, may be a kit including a primer designed such that the primer is capable of amplifying a region containing the mutation site, and further including one of or a combination of reagents necessary for detecting the mutation. The reagent may be a probe, a restriction enzyme, a reagent for use in a method of determining a base sequence (such as the Maxam Gilbert Method, Sanger method and the like), or the like reagent, which is designed to be capable of performing the detection as to the mutation. Note that the reagent may be adopted arbitrarily according to which one of the method of detecting is adopted. For example, the reagent may be dATP, dUTP, dTTP, dGTP, a DNA synthetic enzyme, an RNA synthetic enzyme, or the like. Furthermore, the kit may include an appropriate buffer, washing liquid or the like, which does not hinder the detection of the mutation.

In case of the kit including the primer, the primer is not particularly limited, provided that the primer is capable of amplifying the region containing the mutation site. For example, the primer may be a set of the primers shown in SEQ. ID NOs. 3 and 4.

Moreover, the kit for detecting whether the protein has the mutation or not may be, for example, a kit including the antibody that recognizes only the glycine-insertion type protein.

As descried above, it is possible to perform the diagnosis of RA (to evaluate onset or onset possibility of RA) with high accuracy by using those evaluation kits.

(3) Use of Normal Type Protein or the like in Remedy and Curing Medicine for RA

As described above, the mutation in which 3 bases are inserted into Angiopoietin-1 gene (and the corresponding mutation in which glycine is inserted into an amino acid sequence) is considered as one cause of onset of RA. Therefore, it is considered that it is effective to supplement the normal type protein (that is, glycine deletion type protein to the RA patient having the mutation in which glycine is inserted into Angiopoietin-1. Thus, the present invention provides the following remedy and curing medicine for RA.

A remedy for rheumatoid arthritis, comprising the steps of supplementing, to a rheumatoid arthritis patient having a protein having the mutation, (a) a normal type protein not having the mutation, (b) DNA coding the normal type protein, or (c) a low molecular weight compound that acts as an agonist for a receptor protein for which the normal protein is a ligand;

A curing medicine for use in curing a rheumatoid arthritis patient having a protein having the mutation, the curing medicine containing, as a main component, (a) a normal type protein not having the mutation, (b) DNA coding the normal type protein, or (c) a low molecular weight compound that acts as an agonist for a receptor protein for which the normal protein is a ligand.

How to supplement the normal type protein is not particularly limited. For example, a well-known protein-expression system or a gene-introduction method may be employed. Specifically, an expression vector, a virus vector, or the like, which is used for expressing a protein in a mammalian cell, may be adopted. Moreover, as descried above, Angiopoietin-1 is a ligand for TIE2 receptor. Hence, it is consider to be an effective remedy for RA, to administrate a low molecular weight compound into body orally or by intravenous injection, the low molecular weight compound acting as an agonist for TIE2 receptor. Note that the low molecular weight compound discussed here may be a protein such as peptide or the like.

Moreover, the normal protein or DNA coding the normal protein, and the low molecular weight compound as the agonist for the TIE2 receptor may be used solely or in combination as the curing medicine.

BRIEF DESCRIPTION OF DRAWINGS

FIG. 3(a) shows a result of sequence analysis on a gene of 3-base-insertion type (SEQ. ID NO.:10), whereas FIG. 3(b) shows a result of sequence analysis on a gene of 3-base-deletion type (SEQ. ID NO.:11).

BEST MODE FOR CARRYING OUT THE INVENTION

One embodiment of the present invention will be described below referring to FIGS. 1 to 6. Note that the present invention is not limited to the description below.

(1) Genetic Analysis using Microsatellite Markers

Chain length analysis was conducted for 33 families each of which included two patients and one healthy subject. From DNA extracted from peripheral blood, microsatellite markers, D8S176, D8S521, D8S1738, D8S556, D8S1830, and D8S539 on Chromosome 8 were amplified by the PCR method using a fluorescent labeled primer, D8S176, D8S521, D8S1738, D8S556, D8S1830, and D8S539 having heterozygosity of 0.7 or more and being located within 10.8cM from the aforementioned microsatellite marker D8S556. Then, the amplified microsatellite markers was subjected to electrophoresis 3000V for two hours by using ABI377-model sequencer. After that, sizes of the markers were determined by using Gene Scan (ver.2.0.2). Subsequently, by using MAPMAKER/SIBS(ver.2.1) (see Complete multipoint sib-pair analysis of quantitative and qualitative traits. Am. J. Hum. Genet. 57: 439, 1995), Maximum Lod scores thereof were calculated out via two-point analysis based on the affected sib-pair method.

Figures 1, 2:
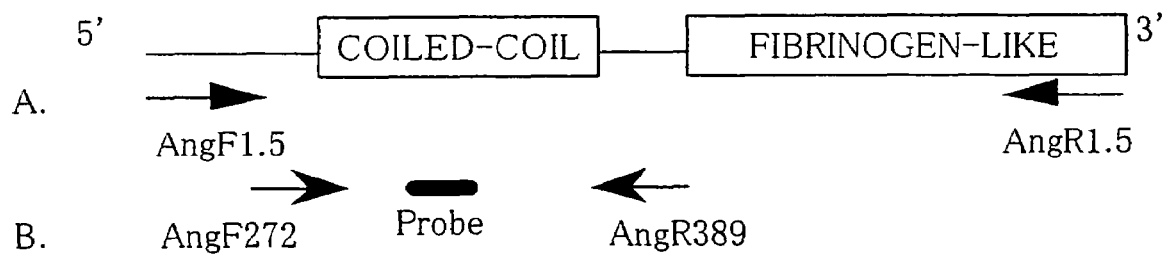
FIG. 1 is a table showing genetic analysis conducted by using 6 kinds of microsatellite markers in a present example.
FIG. 2 is a schematic diagram schematically illustrating an RA-related gene of the present invention. Note that, in FIG. 2, A and B show where a primer and a probe used in the present example were set.
Figure 3:
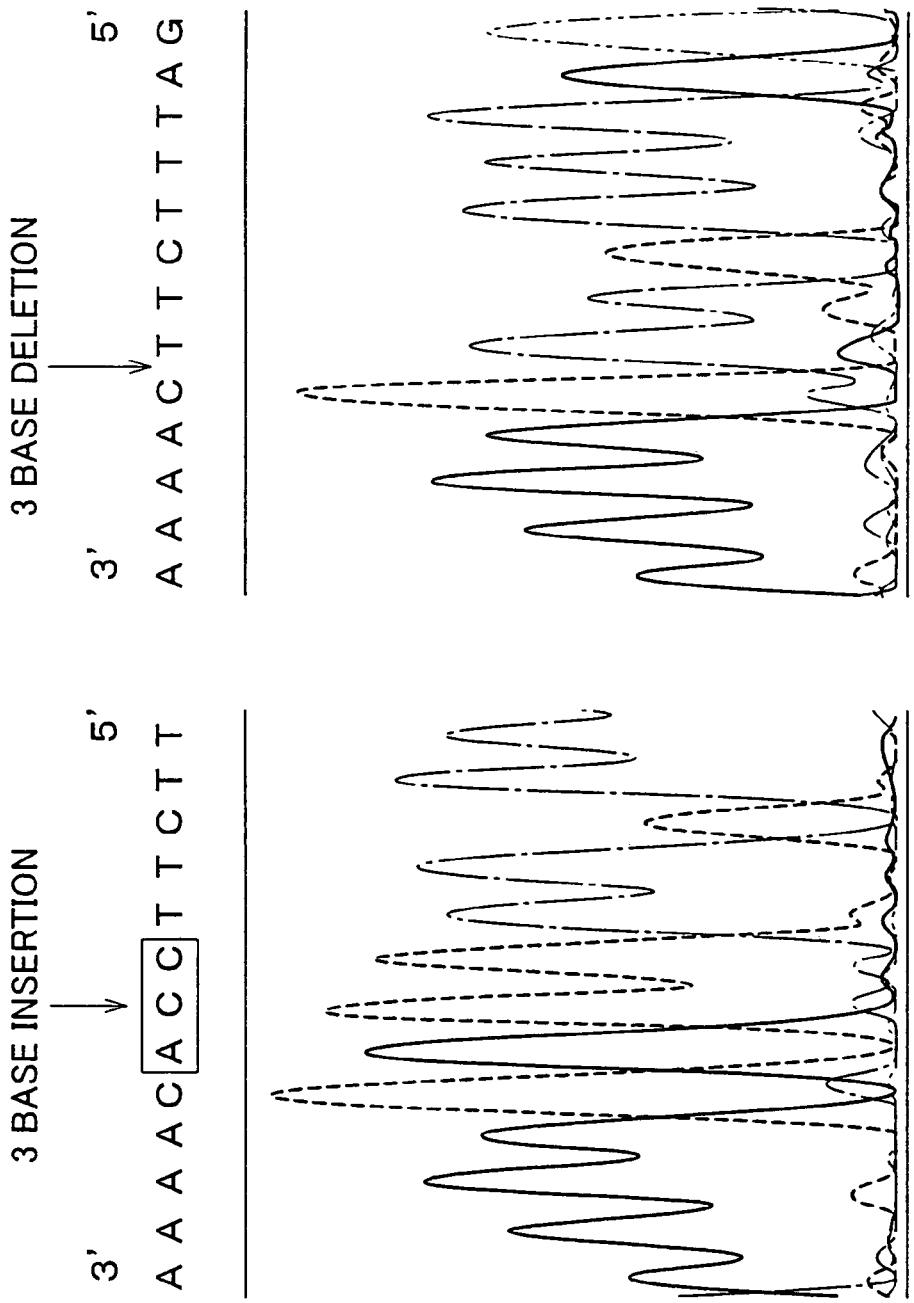
FIGS. 3(a) and 3(b) are views showing results of sequence analysis on a 3-base-insertion-mutation-site-containing region of the RA-related gene.

Results are shown in the Table of FIG. 1. As shown in FIG. 1, a largest Lod Score, 1.35, was observed solely at D8S556. From this result, it was found that an RA-related gene according to the present invention has linkage with the microsatellite marker D8S556. Moreover, from the fact that Angiopoietin-1 is located in the vicinity of D8S556, and the like facts, it is deduced that above-mentioned Angiopoietin-1 is a candidate gene for the RA susceptibility gene.

(2) Sequence Analysis of Angiopoietin-1 cDNA

By reverse transcription reaction using an Oligo dT primer (GeneAmp RNA PCR Kit)(Applied Biosystems), cDNA was synthesized from a total RNA prepared from a monocyte fraction in the peripheral blood of the RA patient and from a synovial cell of the RA patient. After amplifying a gene region of Angiopoietin-1, 1508 bp, a sequence analysis was conducted following the dye terminator method. Note that the primer used in the reaction are listed below:

```
Sense Primer:
AngF1.5:
5'-GCTGGCAGTACAATGACAG-3'    (SEQ. ID NO: 3)

Anti Sense Primer:
AngR1.5:
5'-TCAAAAATCTAAAGGTCGAAT-3   (SEQ. ID NO: 4)
```

Moreover, the sense primer AngF1.5 and the anti sense primer AngR1.5 were positioned as indicated by A. in FIG. 2. Note that the molecule of Angiopoietin-1 had a coiled-coil domain and a fibrinogen-like domain.

The cDNA sequence determined by sequencing was compared with a previously reported sequence (accession No. U83508) of the Angiopoietin-1 gene. As a result, it was found that there were two types of Angiopoietin-1 gene as described above, namely 3-base-insertion type and 3-base-deletion type. Of these types a gene sequence of the 3-base-insertion type was shown in SEQ. ID NO. 2. As shown in SEQ. ID NO. 2, 3 bases "GGT" are inserted as bases No. 805 to No. 807 in the sequence of the 3-base-insertion type.

FIGS. 3(a) and 3(b) show results of sequence analysis of a region containing mutation site. FIG. 3(a) shows the result of the analysis of the 3-base-insertion type, whereas FIG. 3(b) shows the result of the analysis of the 3-base-deletion type (3 base depletion type). Note that FIGS. 3(a) and 3(b) show the results of the sequence analysis of complementary sequences of the gene sequences. From FIG. 3(a), it was confirmed that insertion of 3 bases "GGT" occurred in the 3-base-insertion type (insertion of 3 bases "ACC" in the complementary sequence). From FIG. 3(b), it was confirmed that these 3 bases are lost in the 3-base-deletion type.

As shown in SEQ. ID NO. 1, glycine is inserted as a 269th amino acid in an amino acid sequence of a protein produced by translation of the 3-base-insertion type of gene. On the other hand, this glycine as the 269th amino acid is deleted in a protein produced from translation of the 3-base-deletion type of gene.

(3) Detection of the Mutation in RA Patients and Healthy Subject (a Person who has not Developed RA)

Detection was carried out whether the mutation of 3 base insertion was present or absent in (a) RA patients from families (hereinafter, referred to as RA families) which had another RA patient in kin besides the RA patient himself, (b) healthy subjects from the RA families, (c) RA patients from families (hereinafter, referred to as Sporadic families) which had no other RA patient than the RA patient himself, and (d) healthy subjects from the Sporadic families.

The detection was carried out by (1) extracting genomic DNA from the peoples to be tested, (2) amplifying the region containing the mutation site by the PCR reaction in which an appropriate primer was used, (3) performing sequence analysis of resultant PCR products. Note that as the appropriate primer, one of a sense primer and anti sense primer may be arbitrarily used, with which amplification of the region containing the mutation of 3 base insertion can be carried out. Moreover, there is no particular limitation as to how long the appropriate primer is, provided that amplification of untargeted region will not occur as a result of mismatching. In general, a primer having a length of 15 to 25 nucleotides is used. The following oligonucleotides are examples of the sense primer and the anti sense primer.

```
Sense Primer:
5'-CAACCTTGTCAATCTTTGC-3'    (SEQ. ID NO.5)

Anti Sense Primer:
5'-ACACCTTTTTGGGTTCTGGC-3'   (SEQ. ID NO.6)
```

Figures 4, 5:
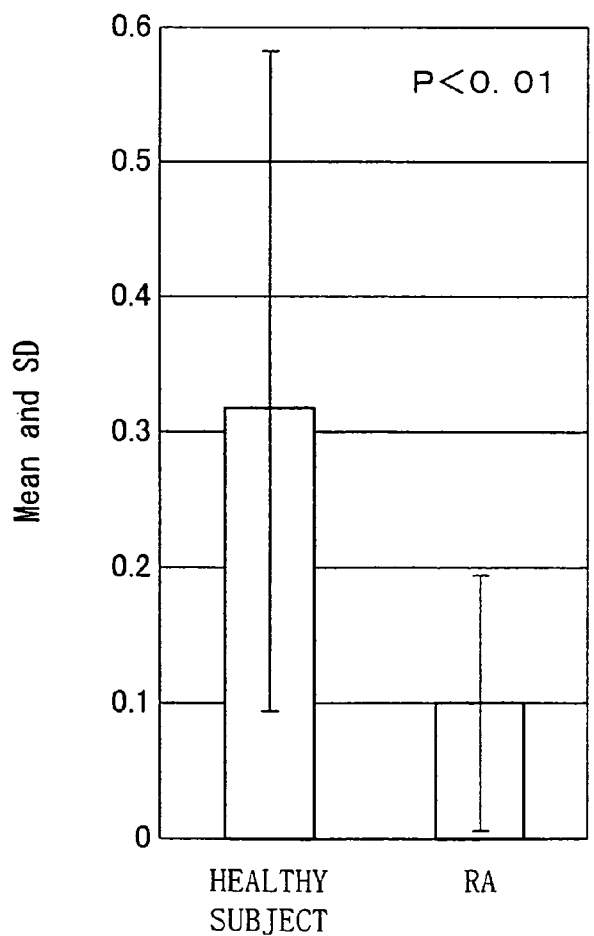
FIG. 4 is a table showing results of detection, carried out in the present example, to find out whether the 3 base insertion mutation occurred or not in RA patients and healthy subjects.
FIG. 5 is graph showing a quantitative analysis of mRNA expression in the present example.

Results of the mutation detection according to the method are shown in FIG. 4. In FIG. 4, "Familial RA" indicates the RA patients from the RA families, "Familial not RA" indicates the healthy subjects from the RA families, "Sporadic RA" indicates the RA patients from the Sporadic families, and "Sporadic not RA" indicates the healthy subjects from the Sporadic families. Moreover, "n" indicates a total number of each type of the peoples tested. The respective columns respectively show numbers of people (in FIG. 4, indicated as "nt805(del3) homo") having the normal gene homologously, numbers of people (in FIG. 4, indicated as "nt805(del3) hetero") having the mutation gene homologously, and numbers of people (in FIG. 4, indicated as "nt805 homo") having the mutation gene homologously. Further, ratios of the people over the number of the people tested shown in parenthesis.

As shown in FIG. 4, both in the RA families and the Sporadic families, only the RA patients have the 3-base-insertion type gene homozygously. Moreover, where it is put that the 3-base-deletion type homozygotes is not mutated, heterozygotes and the 3-base-insertion type is mutated, there found a significant difference between the RA patients from the Sporadic families and the healthy subjects from the Sporadic families, and between the RA patient from the Sporadic families and the healthy subjects from the RA families. This finding confirmed that the onset of RA is in relation with whether the mutation is present or absent.

Therefore, by detecting, using the above method, whether or not the 3 base insertion mutation occurs in the RA relating gene, it is possible to evaluate whether or not RA onset has occurred in a person, or whether or not a person has a possibility of RA onset. Specifically, for example, a subject is tested for detection of the 3 base insertion mutation according to the method. If only the mutation gene is detected (that is, the subject has the mutation gene homozygously), or both the mutation gene and the normal gene are detected, it is evaluated that there is a high possibility that the subject has developed RA. Moreover, in case where the detection detects no mutation gene (that is, the person tested has the normal gene homozygously), it is evaluated that there is a low possibility that the subject has developed RA or will develop RA in the future. Note that to which the evaluation according to the present invention is not limited to the aforementioned way, and the evaluation according to the present invention may be carried out arbitrarily in other ways in accordance with the data of the detection.

(4) Quantitative Analysis of mRNA of the RA Relating Gene

An amount of expressed Angiopoietin-1 mRNA in peripheral blood was measured for twenty one RA patients and eighteen healthy subjects by performing Quantitative RT-PCR with ABI7700 by using TaqMan EZ RT-PCR kit (Applied Biosystems). The following primers and probe were used. GAPDH was an internal standard. Note that positions of the primers and probe are indicated by B. in FIG. 2.

```
Sense Primer AngF272:
5'-TTTGCGAGAGGCACGGAA-3'         (SEQ. ID NO. 7)

Anti Sense Primer AngR389:
5'-TATATCTTCTCCCACTGTTT-3'       (SEQ. ID NO. 8)

Probe Taq Man Probe:
5'-TTCCTCGCTGCCATTCTGACTCACATA-3' (SEQ. ID NO. 9)
```

The results of the quantitative analysis were calculated as relative amounts being in a ratio with the internal standard, and then statistically calculated by Welch's t-test. FIG. 5 is a graph showing an average value and a standard deviation of the quantitatively analyzed amount of the expressed mRNA extracted from the peripheral blood of the healthy subject (control) and RA patients. The results are shown below as averages±standard deviations.

Healthy Subjects: 0.3372±0.2421
RA Patients: 0.0986±0.0937

The above results confirmed that the RA patients have a significantly small amount of expressed Angiopoietin-1 mRNA compared with the healthy subjects.

Therefore, by measuring the amount of the expressed mRNA by the method, it is possible to evaluate whether a person tested has developed RA or not. Specifically, for example, two threshold values (threshold values 1 and 2) are set with respect to the amount of the expressed mRNA. If the amount of the expressed mRNA is equal to or less than the threshold value 1, it is judged that the person tested has developed RA highly possibly or have a high possibility that he will develop RA onset in the future; if the amount of the expressed mRNA is equal to or more than the threshold value 2, it is judged that the person tested has developed RA unlikely or have a low possibility that he will develop RA onset in the future. It is preferable that the threshold value 1 is set to be equal to or less than an average value (that is, 0.0986 or less) of the RA patients. Moreover, it is preferable that the threshold value 2 is set to be equal to or more than an average value (that is, 0.3372 or more) of the healthy subjects.

(5) Comparison between the 3-base-insertion Type (Mutation Type) and the 3 Base Deleted (Wild Type) of Angiopoietin-1 Gene in Terms of Physiological Function Next, the 3-base-insertion type and 3-base-deletion type of Angiopoietin-1 gene (Ang1) were compared in terms of physiological function. In the 3-base-insertion type of Angiopoietin-1 gene (Ang1), the 3 bases were inserted, whereas in the 3-base-deletion type of Angiopoietin-1 gene (Ang1) the 3 bases were deleted. The comparison in terms of the physiological function was conducted by measuring a migration ability of HUVEC cell by using a method explained below.

Human fibronectin (Becton, Dickinson and Company: #354008) of final concentration of 50 µg/ml is coated on a membrane (pore size: 8.0 µg) having transwell-24 (Coster Inc.: #3422). The transwell is two-layered in order to measure the migration ability of cells. Counted as a migration cell number is a number of cells migrated to a lower layer from an upper layer on which the cells are inoculated. 25,000 HUVEC cells suspended in 100 µl of M199 with 1% BSA were inoculated per one transwell. Into each transwell, added was 600 µl of a supernatant of a culture of SVS cell (J. Mol. Cell. Cardiol., 29(8), 1997, 2177-2186) into which the 3-base-insertion type Ang1 or the 3-base-deletion type Ang1 was introduced, the culture prepared by two-day incubation in M199 with 1% BSA.

After incubating the transwells for 6 hours, fixation and dyeing of the cells were carried out by standard methods known in the art. Then, numbers of cell migrated to a lower surface of the membrane were counted for the 3-base-insertion type and the 3-base-deletion type respectively. By using an inverted microscope, counting was so conducted by taking 6 views per well with 40 times magnification. A total (A) and an average (B) of the counting were found. This counting was conducted for 6 wells and average and standard deviation of the 6 wells were calculated out. Results of the counting are shown below. Moreover, FIG. 6 shows averages of numbers of migrated cell respectively for 3-base-insertion type (Ang1) and 3-base-deletion type (Ang1(del3)).

Results:

|  | Average Value (A/B) | Standard Deviation (A/B) |
| --- | --- | --- |
| 3-base-deletion type | 260/43 | 41/7 |
| 3-base-insertion type | 520/87 | 81/14 |

Figure 6:
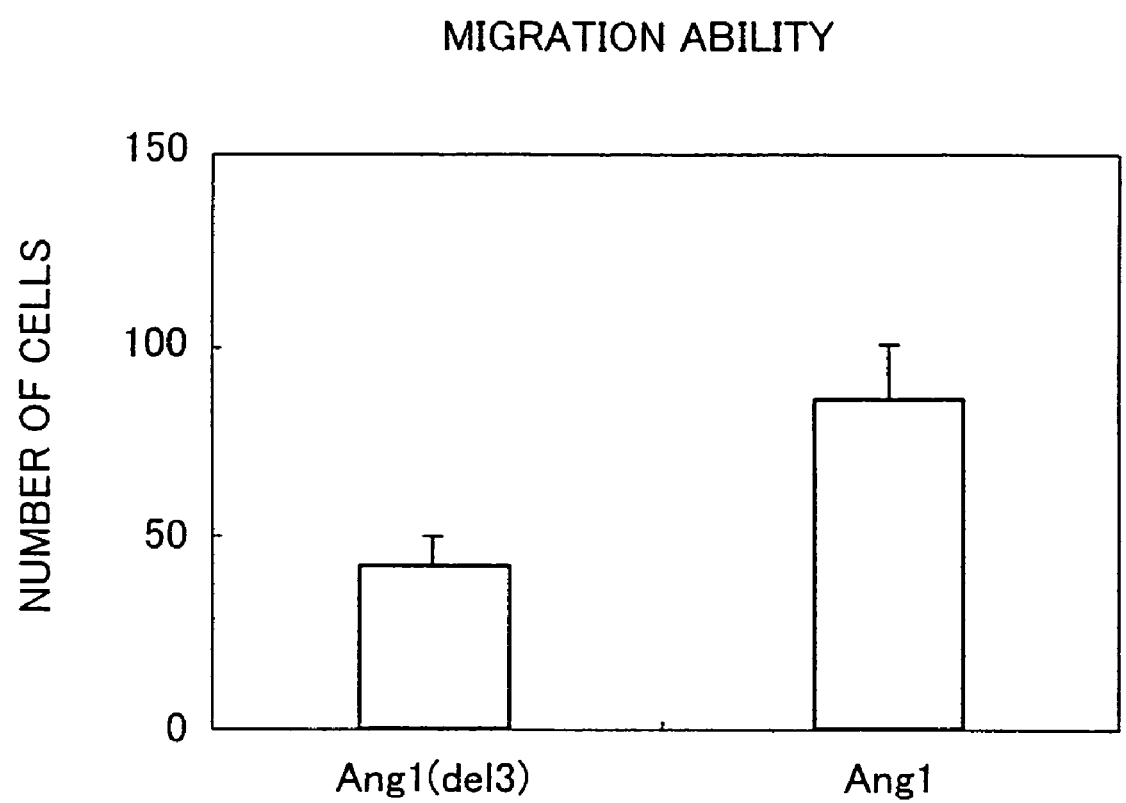
FIG. 6 is a graph showing a result of measuring migration abilities of HUVEC cells of the 3-base-insertion type (Ang1) and the 3-base-deletion type (Ang1(del3)).

As shown in the above results and FIG. 6, it was confirmed that the migration ability of HUVEC cells is significantly high in the mutation type in which 3 bases are inserted into Ang1. This results suggest that the 3-base-insertion type Ang1 is a factor of synovial growth by improving angiogenesis more than in a healthy type.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

As described above, according to the present invention, use of a mutated gene or a mutated protein makes it possible to surely and easily evaluate, with high accuracy, onset or onset possibility of rheumatoid arthritis by detecting whether the mutation is present or absent. Thus, the present invention is effective. Further, the present invention is effective as a novel prevention method, a novel remedy, and a novel curing medicine, for rheumatoid arthritis.

The invention claimed is:

1. A method of evaluating onset possibility of rheumatoid arthritis in a human subject, the method comprising the steps of:

detecting whether a gene coding a protein comprising the amino acid sequence of SEQ. ID NO.:1 is present homozygously in the subject; and evaluating the onset possibility of rheumatoid arthritis in the subject; wherein the homozygous presence of the gene in the subject is indicative of an increased possibility of onset of rheumatoid arthritis in the subject.

2. The method of claim 1, wherein the rheumatoid arthritis is sporadic rheumatoid arthritis.

* * * * *

SEQUENCE LISTING

<160> NUMBER OF SEQ ID NOS: 9

<210> SEQ ID NO 1
<211> LENGTH: 498
<212> TYPE: PRT
<213> ORGANISM: Homo sapiens

<400> SEQUENCE: 1

```
Met Thr Val Phe Leu Ser Phe Ala Phe Leu Ala Ala Ile Leu Thr His
  1               5                  10                  15

Ile Gly Cys Ser Asn Gln Arg Arg Ser Pro Glu Asn Ser Gly Arg Arg
             20                  25                  30

Tyr Asn Arg Ile Gln His Gly Gln Cys Ala Tyr Thr Phe Ile Leu Pro
         35                  40                  45

Glu His Asp Gly Asn Cys Arg Glu Ser Thr Thr Asp Gln Tyr Asn Thr
     50                  55                  60

Asn Ala Leu Gln Arg Asp Ala Pro His Val Glu Pro Asp Phe Ser Ser
 65                  70                  75                  80

Gln Lys Leu Gln His Leu Glu His Val Met Glu Asn Tyr Thr Gln Trp
                 85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
    130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
        195                 200                 205

Leu Asp Thr Leu Lys Glu Glu Lys Glu Asn Leu Gln Gly Leu Val Thr
    210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Gly Val Leu Leu
            260                 265                 270

Lys Gly Gly Lys Arg Glu Glu Glu Lys Pro Phe Arg Asp Cys Ala Asp
        275                 280                 285

Val Tyr Gln Ala Gly Phe Asn Lys Ser Gly Ile Tyr Thr Ile Tyr Ile
    290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
                325                 330                 335

Phe Gln Arg Gly Trp Lys Glu Tyr Lys Met Gly Phe Gly Asn Pro Ser
            340                 345                 350

Gly Glu Tyr Trp Leu Gly Asn Glu Phe Ile Phe Ala Ile Thr Ser Gln
```

```
                355                 360                 365
Arg Gln Tyr Met Leu Arg Ile Glu Leu Met Asp Trp Glu Gly Asn Arg
    370                 375                 380

Ala Tyr Ser Gln Tyr Asp Arg Phe His Ile Gly Asn Glu Lys Gln Asn
385                 390                 395                 400

Tyr Arg Leu Tyr Leu Lys Gly His Thr Gly Thr Ala Gly Lys Gln Ser
                405                 410                 415

Ser Leu Ile Leu His Gly Ala Asp Phe Ser Thr Lys Asp Ala Asp Asn
                420                 425                 430

Asp Asn Cys Met Cys Lys Cys Ala Leu Met Leu Thr Gly Gly Trp Trp
            435                 440                 445

Phe Asp Ala Cys Gly Pro Ser Asn Leu Asn Gly Met Phe Tyr Thr Ala
450                 455                 460

Gly Gln Asn His Gly Lys Leu Asn Gly Ile Lys Trp His Tyr Phe Lys
465                 470                 475                 480

Gly Pro Ser Tyr Ser Leu Arg Ser Thr Thr Met Met Ile Arg Pro Leu
                485                 490                 495

Asp Phe

<210> SEQ ID NO 2
<211> LENGTH: 1497
<212> TYPE: DNA
<213> ORGANISM: Homo sapiens

<400> SEQUENCE: 2
atgacagttt tcctttcctt tgctttcctc gctgccattc tgactcacat agggtgcagc        60
aatcagcgcc gaagtccaga aaacagtggg agaagatata accggattca acatgggcaa       120
tgtgcctaca ctttcattct tccagaacac gatggcaact gtcgtgagag tacgacagac       180
cagtacaaca caaacgctct gcagagagat gctccacacg tggaaccgga tttctcttcc       240
cagaaacttc aacatctgga acatgtgatg aaaattata ctcagtggct gcaaaaactt       300
gagaattaca ttgtggaaaa catgaagtcg gagatggccc agatacagca gaatgcagtt       360
cagaaccaca cggctaccat gctggagata ggaaccagcc tcctctctca gactgcagag       420
cagaccagaa agctgacaga tgttgagacc caggtactaa atcaaacttc tcgacttgag       480
atacagctgc tggagaattc attatccacc tacaagctag agaagcaact tcttcaacag       540
acaaatgaaa tcttgaagat ccatgaaaaa acagtttat tagaacataa aatcttagaa       600
atggaaggaa aacacaagga gagttggac accttaaagg aagagaaaga gaaccttcaa       660
ggcttggtta ctcgtcaaac atatataatc caggagctgg aaaagcaatt aaacagagct       720
accaccaaca acagtgtcct tcagaagcag caactggagc tgatggacac agtccacaac       780
cttgtcaatc tttgcactaa agaaggtgtt ttactaaagg aggaaaaag agaggaagag       840 aaaccattta gagactgtgc agatgtatat caagctggtt ttaataaaag tggaatctac       900
actatttata ttaataatat gccagaaccc aaaaaggtgt tttgcaatat ggatgtcaat       960
gggggagggt ggactgtaat acaacatcgt gaagatggaa gtctagattt ccaaagaggc      1020
tggaaggaat ataaaatggg ttttggaaat ccctccggtg aatattggct ggggaatgag      1080 tttattttg ccattaccag tcagaggcag tacatgctaa gaattgagtt aatggactgg      1140
gaagggaacc gagcctattc acagtatgac agattccaca taggaaatga aaagcaaaac      1200
tataggttgt atttaaaagg tcacactggg acagcaggaa acagagcag cctgatctta      1260 cacggtgctg atttcagcac taaagatgct gataatgaca actgtatgtg caatgtgcc      1320
```
ctcatgttaa caggaggatg gtggtttgat gcttgtggcc cctccaatct aaatggaatg    1380
ttctatactg cgggacaaaa ccatggaaaa ctgaatggga taaagtggca ctacttcaaa    1440
gggcccagtt actccttacg ttccacaact atgatgattc gacctttaga ttttga       1497

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthesized
      oligonucleotide

<400> SEQUENCE: 3
gctggcagta caatgacag                                                  19

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:Synthesized
      oligonucleotide

<400> SEQUENCE: 4
tcaaaaatct aaaggtcgaa t                                               21

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:Synthesized
      oligonucleotide

<400> SEQUENCE: 5
caaccttgtc aatctttgc                                                  19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:Synthesized
      oligonucleotide

<400> SEQUENCE: 6 acacctttttt gggttctggc                                                20

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:Synthesized
      oligonucleotide

<400> SEQUENCE: 7
tttgcgagag gcacggaa                                                   18

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:Synthesized

```
        oligonucleotide

<400> SEQUENCE: 8
tatatcttct cccactgttt                                              20

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence:Synthesized
        oligonucleotide

<400> SEQUENCE: 9
ttcctcgctg ccattctgac tcacata                                      27
```